United States Patent [19]

Nagamatsu et al.

[11] Patent Number: 5,032,281

[45] Date of Patent: Jul. 16, 1991

[54] SEPARATING MEMBRANE AND SEPARATION METHOD

[75] Inventors: Shinji Nagamatsu; Yoshikazu Tanaka; Tohru Shibata, all of Hyogo, Japan

[73] Assignees: Daicel Chemical Industries, Ltd.; Tanabe Seiyaku Co., Ltd., both of Osaka, Japan

[21] Appl. No.: 556,293

[22] Filed: Jul. 20, 1990

[30] Foreign Application Priority Data

Aug. 9, 1989 [JP] Japan .................................. 1-206336
Dec. 7, 1989 [JP] Japan .................................. 1-320141

[51] Int. Cl.$^5$ ...................... B01D 61/14; B01D 61/24
[52] U.S. Cl. .................................. 210/651; 210/654; 210/500.37

[58] Field of Search ...................... 210/500.21, 500.22, 210/500.27, 651, 650, 649, 652–654, 500.37, 500.38, 500.39

[56] References Cited

U.S. PATENT DOCUMENTS 4,261,834 4/1981 de Winter .......................... 210/651

Primary Examiner—Frank Sever
Attorney, Agent, or Firm—Flynn, Thiel, Boutell & Tanis

[57] ABSTRACT

A separating membrane having a porous membrane structure with a pore size distribution such that the membrane does not permeate 90 percent or more of particles having a size of 0.5 micron when the membrane is 0.1 mm thick. The membrane is composed of a material having a nitrogen-containing compound and is liquid-permeable to adsorb and retain phosphopolyols contained in a liquid.

8 Claims, No Drawings

SEPARATING MEMBRANE AND SEPARATION METHOD

The invention relates to a membrane for separation of phosphopolyal substances (PPS), such as toxic pyrogens, from liquids introduced directly into a living body such as injecions, dialysing fluids and infusions and also to diluting water and washing water used in the field. The membrane of the invention may be applied to an organic solvent for the same purpose. It can adsorb DNA and RNA in the field of gene technology. It is useful for adsorption of PPS from bacterium and animal cells.

The phosphopolyol (PPS) is a compound composed of a phosphoric acid moiety and a polyol moiety, such as LPS, lipid A, nucleic acid and a glycerol phosphate compound. Many such polyol compounds have physiological activity. They, even in small amounts, can be removed by the invention.

The invention relates moreover to a method for separating pyrogens from a liquid by way of the membrane.

PRIOR ART

An adsorbent and a separating membrane are both used for the purpose of separating substances contained in a liquid. The relative difficulty of separation processes necessitated in the industry varies depending upon various factors such as kinds of substances contained in the system, separating power and throughput. Removal of a pyrogen is an example of a separation process wherein the severity of its requirements is especially high. Examples of a technical field similar thereto includes the removal of a nucleic acid and other PPS.

Examples of the liquid from which a pyrogen should be removed include liquids directly introduced into a living body without passing through a digestive tract, such as liquid medicines for injection, nutrient infusion, and dialysis, as well as diluent water for these medicines; apparatuses for handling the above-described liquids; and wash water for containers of the above-described liquids.

A pyrogen is a substance that produces an abnormal increase in body temperature of homeotherms even in a very small amount. When the pyrogen enters into blood as a contaminant of an intravenous injection, etc., there occurs a severe fever independently of the effect of the drug. It is believed that when the above-described action is excessive, there occurs a fever attended with a shaking chill and, in some cases, shock death. Bacterial substances, inflammatory substances, vegetable polysaccharides, blood group substances or the like are known as pyrogens. Among them, bacterial substances are most deeply involved in fever and called a bacterial toxin, which is broadly classified into an exotoxin and an endotoxin. Among the above-described toxins, the endotoxin, as the so-called O antigen composed mainly of a cell wall lipopolysaccharide (LPS) of Gram-negative bacteria, has the strongest pyrogenic property and cannot be deactivated even by heat treatment. Once the endotoxin is incorporated into a liquid by chance, it is very difficult to remove. Thus, pyrogens are used equally to endotoxins or LPS.

Chemical decomposition, membrane separation, gel filtration, adsorption, etc. are known as methods of removing a pyrogen. The applicability of chemical decomposition is limited due to the resistance of a substance to be treated in a decomposer, problems derived from contamination by a decomposer and a decomposition product, etc.

Membrane separation and gel filtration can be regarded as a separation method wherein a difference in the size between the pyrogen and the substance to be treated is utilized. Regarding the size of the pyrogen, the variety of pyrogens, the association of LPS and the presence of lipid A should also be taken into account. Specifically, even when the matter is limited to LPS, which is the most important substance among various pyrogens, an aliphatic chain of the portion involved in the pyrogenic action, i.e., lipid A, and a polysaccharide bonded thereto are each specific and vary in kind according to the kind of bacteria as an origin of LPS. An LPS having a molecular weight of about 5000 associates to form a large micellar structure having a molecular weight as large as several millions, while lipid A, having a molecular weight of about 2000 per se, is a pyrogen.

An ultrafiltration membrane (UF membrane) and a reverse osmosis membrane (RO membrane) are used for the removal of a pyrogen by means of a membrane. An apparatus comprising a plurality of membranes has also been proposed for the purpose of attaining a low pyrogen content for pyrogen removing processes which use membranes. Examples thereof include apparatuses disclosed in Japanese Patent Laid-Open No. 207517/1982 and U.S. Pat. No. 4,261,834 (by deWinter). When the liquid to be treated is an aqueous solution consisting of water and a low molecular weight drug, a separating membrane permeable to the substance to be treated and impermeable to a pyrogen and a pyrogen-containing cell may be selected for use. However, when the molecular weight of the substance to be treated is large, it is not easy to select a membrane which permits the substance to be treated to permeate therethrough in a good recovery while inhibiting permeation of a pyrogen, particularly a pyrogen having a low molecular weight, as well to attain an intended low pyrogen concentration (the pyrogen concentration which does not induce a fever in an animal varies depending upon the kind of pyrogen but is thought to be generally 5 EU (endotoxin unit)/kg or less. It is more difficult to select a membrane successfully usable for removal of a pyrogen from a liquid containing a high molecular weight substance, such as protein, which makes it almost impossible to remove the pyrogen to a satisfactory low level while maintaining a high drug recovery. In general, separation of substances whose molecular weights lie close together cannot be attained through membrane filtration, which renders membranes unsuitable for use in removal of a substance having a broad molecular weight distribution, such as pyrogens.

It is known that an activated carbon and an ion exchange resin have a capability of adsorbing and removing a pyrogen. Further, a material for a porous separating membrane, e.g., a polyolefin, as well has a capability of adsorbing a pyrogen through a hydrophobic bonding force. However, the above-described materials cannot selectively adsorb a pyrogen from a drug-containing liquid to a very low pyrogen concentration and are therefore unsatisfactory as an adsorbent used in obtaining a drug solution from which the pyrogen has been sufficiently removed.

Other materials having a capability of adsorbing a pyrogen are also known. For example, Japanese Patent Laid-Open No. 112888/1984 discloses a method of removing Gram-negative bacteria and cell wall components thereof by means of an amino group-containing fiber. It may be understood that the lowest pyrogen concentration attained in the working examples described in the above-described laid-open specification is 0.014 mg/ml, i.e., 14000 ng (nanogram), with a percentage removal of 86% obtained in the treatment of an aqueous solution containing 0.1 mg/ml of a lipopolysaccharide.

In recent years, an affinity adsorbent capable of specifically adsorbing a pyrogen, and therefore useful for removal of a pyrogen incorporated in a drug-containing liquid, has become commercially available. Representative examples of this type of adsorbent include polysaccharide gels having a nitrogen-containing cyclic compound bonded thereto as disclosed in Japanese Patent Laid-Open No. 183712/1982. These gels are highly appreciated in the art because they have a capability of selectively adsorbing and removing pyrogens having various and broad ranges of molecular weights from an aqueous solution containing a high molecular weight drug such as a protein. The pyrogen concentration described in the above-described laid-open specification reaches 0.1 ng (nanogram)/ml (0.5 EU/ml) or less.

However, even the above-described adsorbent is not omnipotent. The present inventor has found that this type of adsorbent has a limited pressure resistance performance when used for removal of a pyrogen and therefore cannot exhibit a sufficient performance when used under an increased liquid feed pressure condition. In the conventional pyrogen adsorbent, a gel support of a polysaccharide is used as a base material for the adsorbent for the purpose of attaining an effective contact of an adsorption site with a solution. This makes it necessary for the above-described adsorbent to be used under a pressure that the gel can withstand. When the conventional adsorbent is used, an increase in the treatment speed can be attained only by increasing the amount of the adsorbent. Therefore, realization of a pyrogen adsorbent having a further improved performance has been desired for treating a large amount of a liquid at a high speed with a compact apparatus.

U.S. Pat. No. 4,639,513 to Cuno and U.S. Pat. No. 4,663,163 discloses an ion-exchangeable chromatographic carrier composed of cellulose, a carbon chain and a nitrogen-containing group and is in the membrane, which is however a depth membrane having a large pore size. This should not be a membrane filter.

SUMMARY OF THE INVENTION

A purpose of the invention is to provide a separation process usable also for separation of drugs whose molecular weights lie close together, suitable for treatment in a large quantity and having a high separation performance. A specific example of such a separating means is an adsorbent having an excellent capability of selectively adsorbing a pyrogen, capable of attaining a low pyrogen concentration and suitable for use in the treatment of a large quantity of liquid at a high speed.

The invention provides a separating membrane having a porous membrane structure with a pore size distribution such that the membrane does not permeate 90 percent or more of particles having a size of 0.5 micron when the membrane is 0.1 mm thick, is composed of a material having a nitrogen-containing compound and is liquid-permeable to adsorb and retain phosphopolyols contained in a liquid.

It is preferable that the compound is a nitrogen-containing cyclic compound having a pai-electron system or a nitrogen-containing compound having an aliphatic group chain of 3 to 50 carbon atoms.

The invention provides a method for separating phosphopolyols from a liquid containing them, which comprises treating the liquid by permeation through the membrane as defined above. It is particularly useful in the separation of pyrogens.

The pore size of the membrane in general ranges from 1 nm to 20 microns.

The removal extent of the pyrogens can be determined by administering rabbits with a liquid, using the US reference endotoxin (Lot EC-5). The number of rabbits having a fever is calculated. In this test, an administration amount resulting in fever is 5 EU (Endotoxin Unit)/kg. Since a sample of 10 ml is usually administered per 1 kg of the body weight, the administration amount resulting in fever is calculated to 0.5 EU/ml. This value is equal to 0.1 ng (nanogram)/ml for the above shown reference endotoxin.

In the invention, the membrane can remove pyrogens to such an extent that an aqueous solution containing 5000 EU/ml of pyrogens permeates therethrough at a rate of 10 liters/ m2/hour or more and at least one half of the permeated liquid has a pyrogen concentration of 5 EU/ml or less.

(Physical Form)

The first feature of the separating membrane according to the present invention resides in that the separating means used comprises an affinity adsorbent having such a membrane structure that a number of pores are present, i.e., being in the form of a porous membrane. Suitable examples of the membrane in the above-described form include a porous homogeneous fine filtration membrane. This membrane can maintain its strength, has a thickness enough to come into sufficient contact with a permeating liquid, and has a number of pores having such a size and continuity that a liquid containing an intended drug can pass therethrough while contacting with the membrane without encountering with excessive resistance. Other suitable examples include an anisotropic ultrafiltration membrane comprising a thin, dense and microporous skin layer portion and a thick and more coarse core portion having larger pores. The above-described membrane structures are known in the art of the separating membrane. The thickness of the membrane is usually 10 to 1000 μm, particularly 50 to 300 μm. If necessary, it is also possible to use a thicker membrane and a plurality of membranes put on top of another. The pore size is usually in a range found in the so-called ultrafiltration or fine filtration in the art of membrane separation, e.g., a range from 1 nm to 20 μm, preferably from 10 nm to 5 μm, and a particularly commonly used membrane has a pore size of 50 nm to 1 μm. When a pyrogen is to be removed from a solution containing a drug having a large molecular weight, e.g., a protein or polysaccharide, it is a matter of course to select a membrane having a pore size according to the molecular diameter thereof so that the permeation of the drug is not inhibited. The pore size of the membrane is generally expressed in terms of, e.g., a particle diameter having a percentage inhibition of 90% determined from the relationship between the size of the particle not adsorbed on the membrane and the percentage inhibition.

In the present invention, a nitrogen-containing cyclic compound is bonded to a base material constituting the above-described membrane, and a pyrogen contained in a liquid which penetrates the membrane through the pores therein can come into contact with the ligand of the adsorbent (a nitrogen-containing cyclic compound) located at an appropriate distance from the skeleton of the base material. In the case of an anisotropic membrane, if the membrane is brought into contact with a liquid in such a manner that the skin layer is on the upstream side, the pyrogen comes into contact with a ligand when the liquid passes through the skin layer and further can come into contact with the ligand also in the core portion. The presence of a skin layer is favorable because it prevents such a particle as will clog the pore from entering the inside of the membrane. It is a matter of course that the pore diameter of the skin layer should be such that the intended drug can pass therethrough. A plurality of skin layers may be present. In the case of a homogeneous membrane, it is a matter of course that the pyrogen comes into contact with a ligand when the liquid passes through the pore, thus causing the pyrogen to be adsorbed.

A simple method of obtaining a pyrogen adsorbent having the above-described homogeneous membrane or anisotropic membrane structure comprises selecting a membrane comprising a material having a hydroxyl group, an amino group, etc. from commercially available separating membranes having an appropriate structure and pore size and subjecting the selected membrane to such a treatment that a nitrogen-containing cyclic compound is bonded thereto through a chemical reaction while maintaining the form of the membrane.

A porous membrane having a support is also an example of a form of the adsorbent of the present invention. Examples of such a porous membrane include the above-described homogeneous membrane or an anisotropic membrane formed on a nonwoven fabric of a synthetic fiber. In this case, the strength of the membrane is governed by the support, e.g., a porous plastic film or a fibrous product (such as woven fabric, knit or nonwoven fabric). As with the above-described embodiment, the body portion of the membrane comprising a material composed of an insoluble carrier and a nitrogen-containing cyclic compound bonded thereto has a number of pores and a certain thickness and permits the liquid to pass therethrough while maintaining a desired contact without encountering with excessive resistance.

A membrane comprising a porous plastic film as a support and a base material infiltrated thereinto may be used. The support includes a microporous polypropylene film having a large void ratio, being commercially available with trademark "DURAGARD" or "CELGARD".

Examples of the method of preparing the above-described membranes include one which comprises forming a dope of a high molecular weight substance into a desired form, such as a hollow filament or a flat membrane, through a nozzle, a pourer or the like, and removing a solvent through washing or evaporation to prepare a membrane having pores. The step of bonding a nitrogen-containing cyclic compound to a base material may be conducted before or after the formation of the membrane.

A membranous pyrogen adsorbent provided with pores having such a dimension that the permeation of the liquid and the contact of the liquid with the adsorbent are balanced with each other may be prepared also by other methods. For example, a sheet may be formed by making use of a fibrous base material having a very small diameter (1 m or less) to which a nitrogen-containing cyclic compound has been bonded. The membrane forming method per se is similar to the papermaking method. However, unlike ordinary filter paper, the use of a minute fiber makes it possible to prepare a fine filtration membrane having such a pore size as will ensure excellent contact with the liquid which is indispensable to the present invention. Although the thickness of the membrane depends also upon the denseness of the membrane structure, it is usually as described above.

The separating membrane according to the present invention may be prepared also by bonding a nitrogen-containing cyclic compound through a chemical reaction to a base material comprising a previously prepared membrane having an appropriate structure of an appropriate material, e.g., a microfilter of cellulose.

There is no particular limitation on the form of the membrane, and flat membranes, hollow fiber membranes tubular membranes, etc. may be used. The above-described membranes can be suitably applied in the form of a membrane module. Examples of the membrane module include spiral, preat, plate-and-frame, tubular and hollow fiber modules.

Base Material Constituting Membrane

The separating membrane according to the present invention comprises a base material constituting a membrane and a nitrogen-containing cyclic compound bonded thereto. The base material is one which is generally insoluble, i.e., undissolvable, in a liquid to be treated. The solvent is usually water. In special cases, it is also possible to use nonaqueous solvents such as alcohols, acetone, acetonitrile, DMSO and chloroform, or aqueous solutions thereof. It does not matter whether the base material is insoluble or soluble in the course of formation of an adsorbent as long as it becomes insoluble in a final adsorbent having a nitrogen-containing cyclic compound bonded thereto. Many water-insoluble polysaccharide base materials are insoluble also in organic solvents.

The base material is generally a high molecular weight substance and in many cases a linear organic polymer which is in an aggregated state due to intermolecular force. Since the base material is membranous, it substantially appears to extend two-dimensionally. However, because of the thickness, it is essentially three-dimensional. The base material has such a structure that a nitrogen-containing cyclic compound can be directly or indirectly immobilized thereto. For example, it has an active site (e.g., active hydrogen) which can react with a functional group such as a hydroxyl or amino group or other substance.

Specific examples of the base material include polysaccharides (including their derivatives such as aminoalkylated polysaccharides and carboxyalkylated polysaccharides, e.g., cellulose and its derivatives, agarose and its derivatives, crosslinked dextran and its derivatives and chitosan as mentioned in the Japanese Patent Laid-Open No. 183712/1982), synthetic organic polymers (e.g., polyacrylonitrile, polysulfone, polyamide, polyvinyl alcohol, polystyrene and polyacrylic resins, hydroxyalkylated, aminoalkylated and halogenoalkylated polystyrene resins, and polyacrylamide resins as mentioned in the same laid-open specification), and inorganic polymers (e.g., silica gel, glass, e.g., aminopropylated porous glass, and various ceramics). Further, it is also possible to select a base material from water-insoluble carriers described in the Japanese Patent Laid-Open No. 183712/1982. A functional group useful for formation of a bond with a ligand, such as a hydroxyl or amino group, may be introduced into the above-described base materials by various methods such as copolymerization, methylolation or reduction.

The above-described base material constitutes a membrane so as to have a three-dimensional structure and is bonded to a nitrogen-containing cyclic compound directly or through a spacer. A molecular structure comprising a base material, a ligand and a spacer has an important effect, together with a higher order structure such as association of molecules and formation of pores, on the contact of the liquid with the adsorbent. Selection of a proper base material is very important to the practice of the present invention.

Nitrogen-Containing Cyclic Compound

The nitrogen-containing cyclic compound used in the present invention may be the same as those described in the Japanese Patent Laid-Open No. 183712/1982 and is preferably one having a $\pi$-electron system. Specific examples thereof include compounds represented by the formula R—A—X containing a nitrogen-containing cyclic group R having a skeleton of, e.g., imidazole, pyrazole, pyrimidine, pyridazine, pyrazine, purine, acridine, triazole, oxadiazole, tetrazole, indazole, benzotriazole, benzopyridazine, benzopyrimidine, benzopyrazine or naphthyridine. In the formula, A is a single bond, an alkylene group (such as ethylene, butylene or C12) or an alkenylene group and X is a hydrogen atom, an amino group, a hydroxyl group or carboxyl group, provided that the nitrogen-containing cyclic group and the alkylene group may has a substituent (such as carboxyl, oxo, alkyl, hydroxyl, amino or alkoxy).

Specific examples of the heterocyclic compound include histidine, histamine, urocanic acid, uracil, orotic acid, cytosine, 5-methylcytosine, 2-amino-4,6-dimethylpyrimidine, 2-amino-4-hydroxy-6-methylpyrimidine, adenine and 6,9-diamino-2-ethoxyacridine, among which compounds having an imidazole skeleton, e.g., histamine and histidine, are particularly preferred.

Bonding of Base Material to Nitrogen-Containing Cyclic Compound

Bonding of a ligand comprising a nitrogen-containing cyclic compound to a base material constituting a membrane may be generally conducted by carrier bonding, crosslinking, entrapping (lattice type or microcapsule type), among which carrier bonding is generally selected for use. The crosslinking has problems of manifestation of affinity and securing of sufficient flow rate.

The base material may be bonded to the nitrogen-containing cyclic compound directly or through a spacer. The spacer may be the same as that described in the Japanese Patent Laid-Open No. 183712/1982. Representative examples thereof include $NH_2(CH_2)_nNH_2$, $HOOC(CH_2)_nCOOH$ (or corresponding acid anhydride), $NH_2(CH_2)_nCOOH$ and $NH_2(CH_2)_nOH$ (wherein n is an integer of 1 to 12). The presence of a spacer is particularly useful when a network structure comprising a base material is so dense that the access of a pyrogen to an adsorption site is inhibited.

For example, the boding method in which a ligand is directly or indirectly fixed to a carrier comprising a base material constituting a membrane include covalent bonding, ionic bonding, hydrophobic bonding, coordination bonding, etc. Among them, immobilization by means of covalent bond is desirable because it is less susceptible to elimination of the nitrogen-containing cyclic compound. Examples of the covalent bond include amide, ester, ether, amino, imino, sulfide, disulfide and sulfone bonds.

A ligand or a spacer may be bonded to a base material, e.g., by the following method. A base material is activated with a cyanogen halide (e.g., cyanogen bromide), an epoxy compound (e.g., epichlorohydrin or bisoxirane), a halogenoorganic acid halide (e.g., chloroacetyl chloride or tresyl chloride), a dialdehyde (e.g., glutaraldehyde), benzoquinone or the like, and a nitrogen-containing cyclic compound having an amino group, a hydroxyl group, a thiol group or a carboxyl group, and a spacer is then bonded thereto.

The indirect method for bonding or immobilizing wherein use is made of a spacer carrier, include epoxidation (e.g., epichlorohydrin, bisoxirane), dehydration condensation (WSC, EEDO), reductive amination (NaCN+borane, dimethylamine+borane) and thiol activation (PySSPy). In these methods, a carrier spacer derivative having a group, such as an epoxy, carboxyl, amino, hydrazino, formyl or thiol group, is converted into an active intermediate by making use of a condensing agent, an activator (as exemplified within the parentheses given after the description of each method) and then bonded to a ligand having a group such as amino, carboxyl, aldehyde or thiol group.

The adsorbent prepared by the epoxidation is superior to the cyanogen bromide method most commonly used in the art in that the nonspecific adsorption is low by virtue of more stable immobilization of the ligand, which renders the epoxidation preferable in the present invention.

Examples of the immobilization by other methods than covalent bonding include immobilization, by means of ionic bonding, of a nitrogen-containing cyclic compound having a strongly basic substituent to a carrier having a strongly acidic group bonded to the surface thereof (commercially available as the packing for anion chromatography), and bonding of a base material having a surface which has been made hydrophobic by octadecyl, octyl, phenyl or the like, and a ligand having a long-chain alkyl group or a phenyl group bonded thereto through a hydrophobic bonding (dynamic coating).

The immobilization wherein a base material, a spacer and a nitrogen-containing cyclic compound are bonded to each other is described in detail also in the above-described laid-open specification. In the present invention as well, the immobilization of a ligand can be conducted through application of such an already disclosed technique.

The above-described ligand immobilization technique can be applied to processing of a material having a membranous shape described in Example 1 and processing of a material not having a membranous shape as yet shown in Example 3.

The compound having the aliphatic chain is preferred to have 3 to 30 carbon atoms in the chain. The aliphatic chain may be attached to the compound at its terminal, at its middle or at its pendant group. The nitrogen-containing group attached to the compound preferably includes a primary amino, a secondary amino, a tertiary amino, a quaternary ammonium and an imino group. The primary amino, the secondary amino and the imino group ($=NH$) are more preferable, because they are practically basic and are less prevented from steric hindrance to effect the adsorbance property. A compound having a plurality of amino (NH2) group at its terminal is also useful. These chains are derived from conventional raw materials such as epichlorhydrin, glutaric aldehyde, succinic acid, succinic acid derivatives, hexamethylenediamine, guanidine and amino acids. The following aliphatic chains A to D are particularly shown below.

A: —CH$_2$CH(OH)CH$_2$NHR

Examples of R are hydrogen and the following (In brackets is the name of the compound RNH$_2$ or ROH which correspond to R).

C(—NH)NH$_2$[guanidine], (CH2)$_n$ NH$_2$ (n=1-12, e.g., 6) [alkylenediamine], COCH(NH2) (CH2)$_4$NH$_2$ [lysine], COCH(NH2) (CH2)$_3$ NH2 [ornithine], COCH(NH2) (CH2)$_3$ NHC(—NH)NH$_2$[arginine], [natural polyamine having 2 or more primary and secondary amino groups such as spermidine and spermine]

B: —CH$_2$ CH(OH)CH$_2$ NH(CH2)5NHR

Examples of R: (CH2)$_n$ NH$_2$ (n=1-12), (CH2)$_n$ NHC(—NH)NH$_2$ (n=1-12).

C: —CH$_2$ CH(OH)CH$_2$ NHCOCH2CH2CONHR

Examples of R: (CH2)$_n$ NH$_2$ (n=1-12), (CH2)$_n$ NHC(—NH)NH$_2$ (n=1-12).

D: —CH$_2$ CH(OH)CH$_2$ NH (CH2)$_6$NHR

Examples of R: C(—NH)NH$_2$, COCH(NH2) (CH2)$_4$ NH$_2$, (CH2)$_n$NH$_2$ (n=1-12).

The aliphatic nitrogen-containing compound is in particular effective for a liquid having a high ion strength. The compound can be more freely functional than a conventional anion exchange membrane in which the aromatic ring of polystyrene is attached directly to amino group, that is, having no carbon atom in the aliphatic chain in question. The carbon number range of 3 to 50 according to the invention is much less than that of polymyxin, disclosed in Japanese patent publication B Hei 1-16389. This is the reason few important problems will be caused from the physiological point of view when the nitrogen-containing aliphatic group is accidentally introduced into the treated liquid.

Separation Capability

As can be understood from the foregoing description, the separating membrane of the present invention has the capability of adsorbing and separating a pyrogen upon being brought into contact with a liquid passing through pores of the membrane. As described above, the thickness of the membrane is small. Therefore, the contact time is much shorter than that of not only the batch process used with conventional adsorbents but also the column process. For example, when the membrane thickness and the flow rate are 100 μm ($10^{-2}$ cm) and 50 l/m$^2$·hr, respectively, the value corresponding to SV (space velocity, apparent value) in the column process is 500 (per hr). Therefore, the contact time (apparent value) is 7.2 sec (1/500 hr) which is 1/100 or less of SV3 corresponding to a contact time of about 20 min, in the affinity chromatographic column process.

Nevertheless, satisfactory contact of the liquid with the adsorbent can be attained by properly selecting a base material and a nitrogen-containing cyclic compound (and optionally a spacer) and taking a three-dimensional molecular structure comprising the above-described members and an association structure of molecules and a larger stereostructure, i.e., a membranous form having pores. The separating membrane has pores having such a size as will permit a drug to permeate therethrough, and has a capability of selectively separating a pyrogen to obtain a permeated liquid from which the pyrogen has been substantially completely removed, i.e., enables the pyrogen concentration of an aqueous solution containing 5000 to 500 EU/ml of pyrogens to be reduced to 5 EU/ml or less and further to 0.05 EU/ml or less at a permeation rate of 10 liter per m$^2$ per hour or more.

The separating membrane of the present invention can be used also for removal of a pyrogen from a liquid having a higher pyrogen concentration. In this case, the final pyrogen concentration does not often reach that of the above case where the pyrogen is substantially completely removed. However, the removal of a pyrogen contained in a feed liquid is as high as 99% despite a short contact time, which renders this embodiment sufficiently useful for certain applications.

The separating membrane can be distinguished from other separating means in the physical form and chemical structure as well as in the capability of selectively separating substances contained in a liquid through the above-described permeation method, e.g., a capability of removing a pyrogen from a permeating liquid. For example, a filter paper comprising a fiber having a capability of adsorbing a pyrogen functions as an adsorbent when packed in a column and used with a sufficient contact time. However, when a permeation method wherein the contact time is very short is applied, no sufficient capability of removing a pyrogen can be obtained.

The membrane of the invention can selectively adsorb and separate a phosphopolyol such as pyrogen(s) from a solution of a physiologically active substance. The physiologically substance includes, for example, an amino acid such as histidine, alanine and proline, a nucleic acid base such as adenine and cytosine, an antibiotic such as insulin, a vitamin such as flavin, adenine, dinucleotide and FDA, a seroprotein such as albumin and gamma-globulin, an enzyme such as urokinase, asparaginase and lysozyme, an antibody such as immunoglobulin and a vaccine such as flu vaccine. The invention applies to an injection liquid such as dextran, fructose and glucose, a sodium citrate solution for blood transfusion, an intravenous drip and a supplemental liquid for artificial kidneys of the filtration type. The applicable liquid may have different values of ion strength and concentration. The liquid to administer directly to a living body usually has an ion strength of about 0.15, like physiological saline, which can be effectively treated with the membrane of the invention in particular have an aliphatic nitrogen group.

The method for separation of pyrogens according to the invention may depend on the concentration of the pyrogen. A liquid having a relatively low content of pyrogen, for example 500 EU per ml, can be effectively treated with a membrane having a usual thickness. A pyrogen liquid having a high content can be treated with a thick membrane or laminates of membranes, in a manner that the pore size causes an effective separation at the feeding side having the higher concentration and then adsorption causes separation at the discharging side having the lower concentration. This shows one treatment working two ways. No pre-treatment is needed.

As opposed to the particulate adsorbent having a gel structure, the separating membrane of the present invention is in the form of a membrane having a porous structure. Therefore, the apparatus used for bringing a liquid into contact with separating means is not a packed column but usually a membrane module. In this case, the resistance encountering during permeation of a liquid is mainly the membrane resistance and can get ride of a pressure loss caused by the flow of particles. The membrane resistance varies depending upon pore diameter, membrane thickness, etc. and changes according to the property of the liquid to be treated. However, since the membrane can withstand a pressure encountered when used as a fine filtration membrane and an ultrafiltration membrane, no use of special pressure-resistant apparatus is required. Further, even when the membrane is used as a RO membrane in a region where a higher pressure should be applied, it is possible to impart sufficient pressure resistance to the membrane per se.

Thus, the membrane of the present invention can solve the problems of a particulate adsorbent having a gel structure through a reduction in the liquid permeation resistance and an increase in the pressure resistance. The effect attained by the membrane structure is, however, more than that. Some description will now be given via an example of a calculation how pyrogen removing equipment for treating a large quantity of liquid can be realized on a compact scale according to the present invention.

When a column packed with 1 l of a particulate adsorbent having a gel structure is used, if a liquid is treated under a pressure of about 1 kg/cm$^2$G, the liquid feed rate is usually up to about 3 to 10 l/hr. In the adsorbent of the present invention, a membrane having an area of about 1 to 2 m$^2$ can be provided in a module having a volume of 1 l. Therefore, when the permeation rate is 50 l/m$^2$·hr, the liquid feed rate is 50 to 100 l/hr, which enables the throughput to be increased by a factor of about ten over that of the particulate adsorbent through the use of equipment having the same volume. When the operation pressure is further increased, a 100-fold or more increase in the throughput can be expected.

As has been described above, the separating membrane according to the present invention has a very excellent separation capability not only in respect of the volumetric efficiency but also in every respect including the attainable pyrogen concentration and percentage removal. The separating membrane according to the present invention can attain a membrane separation effect as well because it is in the form of a membrane, which promotes its function as an adsorbent. The above-described effect renders the present invention useful for selectively separating and removing substances having an affinity for a nitrogen-containing cyclic compound including pyrogen and nucleic acids (DNA, RNA) from a solution containing a drug having a broad range of molecular weight from a high molecular weight to a low molecular weight, such as protein, and further a solvent per se with high efficiency.

[EXAMPLES]

In the following description, "(wet)" refers to "wet weight".

EXAMPLE 1

Preparation of PVA membrane containing nitrogen-containing aliphatic chain

Three polyvinyl alcohol (PVA) hollow fiber membranes (Kuraray SF-401; a homogeneous membrane having a pore size of about 0.1 μm; 330 μm inner diameter, 125 μm membrane thickness and 5.5 cm effective length) were fixed in a glass tube with an epoxy resin to prepare a miniature module. Then, the hollow fiber membranes are brought into contact with liquids in the order of steps (1) to (5) by making use of the module as prepared above to subject the membrane to various treatments including a chemical reaction of a material constituting the membrane, thereby preparing the AH-PVA membrane adsorbent of the present invention. In this case, the membrane is brought into contact with the liquid by circulating the liquid in and outside the hollow fiber membrane at a flow rate of 20 to 50 ml/min. The temperature is adjusted by immersing the whole module in a water bath.

(1) washing (1M NaCl, pure water), (2) epoxidation (60° C. in 90 ml of 1N NaOH; further 10 ml of epichlorohydrin is added and the system is kept at that temperature for 2 hr), (3) washing (pure water), (4) spacer bonding (40 ml of 0.625% aqueous hexamethylenediamine solution, 60° C., 2 hr), (5) washing (pure water). The AH-RVA membrane for the adsorbent was prepared.

EXAMPLE 2

Preparation of PVA membrane containing histidine

The AH-PVA membrane obtained in Example 1 was treated as follows: (6) epoxidation (at the same condition as that of step (2)), (7) washing (pure water), (8) histidine (His) immobilization (40 ml of 1 mM His, pH 13, 60° C., 2 hr), (9) washing (1M NaCl, pure water), and (10) rendering the membrane per se pyrogen-free (0.2N NaOH in 20% ethanol as a solvent).

Thus, a PVA membrane containing immobilized histidine (HisPVA membrane) as the adsorbent of the present invention is prepared.

Elementary analysis values (%) of AH-PVA and HisPVA are shown below, with those of PVA membrane.

| Sample | Carbon | Hydrogen | Nitrogen |
|---|---|---|---|
| PVA membrane as raw material | 55.14 | 7.92 | 0.02 |
| AH-PVA membrane | 54.92 | 8.00 | 0.17 |
| HisPVA membrane | 54.27 | 7.87 | 0.40 |

EXAMPLE 3

Removal of pyrogens 42 ml of an untreated water including a pyrogen coming from E. coli olll: B4, 1 ng or 5.5 EU, at a concentration of 550 EU/ml is circulated through the HisPVA membrane obtained in Example 2, having an 1.7 cm$^2$ area and incorporated into the miniature module, at a flow rate of 13 ml/min, and the membrane permeation rate is adjusted to 0.2 ml/min (70 l/m$^2$·hr) by means of a pressure cock. The supply pressure is about 0.2 kg/cm$^2$G. The pyrogen concentration of the permeated liquid is measured by making use of Limulus ES-test, Wako (trademark) and Toxinometer-ET-201 (each a product of Wako Wako Pure Chemical Industries Ltd.).

When the amount of the permeated liquid is 22 ml, the pyrogen concentration and percentage removal of pyrogen are 0.055 EU/ml and 99.99%, respectively. Even when an untreated water having a pyrogen concentration of 5000 EU/ml is used, the pyrogen concentration can be reduced to 0.5 EU/ml or less.

For comparison, the same test is conducted by making use of the same PVA hollow fiber membrane miniature module as that used in Example 1 as a starting material in the preparation of the adsorbent. The pyrogen concentration of permeated water and percentage removal of pyrogens obtained by usual membrane separation are 99 EU/ml and 82%, respectively.

EXAMPLE 4

The same treatment as shown in Example 3 is made, except for using tme AH-PVA membrane obtained in Example 1 under the following conditions: a liquid amount of 50 ml and a pyrogen concentration of 3300 EU/ml. When the amount of the permeated liquid is 25 ml, the pyrogen concentration and removal extent are 0.33 EU/ml and 99.99%, respectively. A comparison is made, using the same PVA hollow fiber membrane, with a removal extent of 81% and 627 EU/ml.

EXAMPLE 5

Preparation of MFC containing histidine

A wood pulp is used as a raw material, and 180 g (wet weight) of a 4% suspension of microfibrilated cellulose having a diameter reduced to about 0.4 $\mu$m by a high pressure homogenizer (a product of Daicel Chemical Industries, Ltd.) is suspended in 270 ml of water. 117 ml of a 2N aqueous sodium hydroxide solution and 27 ml of epichlorohydrin are added thereto, and the mixture is stirred at 40° C. for 2 hr. After the completion of the reaction, the mixture is filtered and the residue is washed with water to prepare an epoxidized MFC.

20 g (wet) of the epoxidized MFC is suspended in 120 ml of a 0.625% aqueous hexamethylenediamine solution and stirred at 60° C. for 2 hr. After the completion of the reaction, the mixture is filtered and the residue is washed with water to prepare an aminohexylated MFC (C: 41.90%, N: 0.22%, H: 6.33%; hereinafter referred to as the "AH-MFC"). The AH-MFC is again epoxidized with an aqueous sodium hydroxide solution and epichlorohydrin to prepare an epoxidized AH-MFC. The epoxidized AH-MFC is suspended in 60 ml of a 1 mM histidine (His) solution, and the pH of the suspension is adjusted to 13 with 1N sodium hydroxide and stirred at 60° C. for 2 hr. After the completion of the reaction, the mixture is filtered, and the residue is washed with 1M saline to prepare 21 g (wet) of a MFC containing immobilized histidine (HisMFC) (C: 42.19%, N: 1.99%, H: 6.44%).

EXAMPLE 6

Preparation of flat membrane 3.8 g of a short aromatic polyamide fiber (20 to 24 $\mu$m in diameter, 3 mm in length) is mixed with 800 ml of pure water, and the mixture is pulverized by means of a mixer. Then, 21 g of the HisMFC prepared in Example 3, 44.1 g (wet) of a 3% aqueous suspension of a microfibrilated aromatic polyamide fiber having a diameter of about 0.4 $\mu$m, 12 g of a heat-crosslinked polyamide resin binder and 300 ml of water are added thereto, and the mixture is stirred. The mixed slurry is sucked through an 80-mesh metal gauze. The resultant sheet is pressed and dried on a hot plate to prepare a microfilter (210×260×0.2 mm) containing the HisMFC. This microfilter comprises cellulose as a base material and the His bonded thereto through a spacer and is a pyrogen adsorbent (His content: about 1%) in the form of a flat membrane molded together with other fiber. As is apparent from a percentage inhibition of 20% for a 0.5 $\mu$m polystyrene standard particle, the pore size is of the order of microns.

EXAMPLE 7

Removal of pyrogen by means of flat membrane adsorbent

A microfilter containing the HisMFC prepared in Example 6 is cut out to have a diameter of 13 mm and fixed as a flat membrane within a holder. 10 ml of an untreated water containing 88000 EU/ml of pyrogen (the same as that of Example 3) is filtered under pressure through the membranous adsorbent at a rate of 0.12 ml/min (54 l/m$^2$·hr). The pyrogen concentration of the permeated liquid thus obtained and the percentage removal are 1100 EU/ml and 99%. It can be confirmed that further permeation of substantially the same amount of the untreated water brings about no significant increase in the pyrogen concentration. However, it is also confirmed that when the permeation rate is increased by a factor of about ten (i.e., to 450 l/m$^2$·hr), the pyrogen concentration of the permeated liquid rapidly increases during permeation of substantially the same amount of the untreated water.

When the test is conducted in the same manner as that of Example 4, except that the MFC is used instead of the HisMFC, the pyrogen concentration of the permeated liquid is 84700 EU/ml, i.e., no significant pyrogen removing effect is observed.

EXAMPLE 8

Treatment of pysiological saline

A 0.9% saline including 4630 EU/ml of pyrogens ($\mu$=0.15) is treated with the membrane AH-PVA of Example 4, 1.7 cm$^2$ in area, resulting in 0.08 EU/ml of pyrogens and a removal extent of 99.998%. A comparison by the PVA membrane results in 1120 EU/ml of pyrogens and a removal extent of 76%.

EXAMPLE 9

Treatment of Cytochrome C having a molecular weight of about 12,500

200 ml of 10.0% Cytochrome C including 1130 EU/ml of pyrogens, at a pH of 9.0 and a $\mu$ of 0.02, is treated in the same way as shown in Example 4, using the AH-PVA membrane of Example 1, having an effective surface area of 50 cm$^2$. The circulation rate is 100 ml/min and the flux is 4.5 ml/min. Results are that the treated liquid has a pyrogen content of 0.23 EU/ml, a removal extent of 99.98% and a Cytochrome content of 10.0%. The rabbit test result is negative. A comparison by the PVA membrane results in a removal extent of 45% and a pyrogen content of 622 EU.

EXAMPLE 10

Treatment of human seroalbumin (HSA)

100 ml of 20% HSA at a pH of 6.5, a $\mu$ of 0.07, and including 85 EU/ml of pyrogens is treated with the the AH-PVA membrane module of Example 9, with the results of a pyrogen content of 0.84 EU/ml and a removal extent of 99%. A comparison by the PVA membrane results in 75 EU/ml of pyrogens and a removal content of 12%.

EXAMPLE 11

Treatment of HSA

About 100 ml of 5% aqueous HSA solution having a pyrogen content of 2.54 EU/ml and an ion strength ($\mu$) of 0.02, a pH of 5.2, and germfree, is treated with the His-PVA membrane of Example 2, having an effective surface area of 50 cm$^2$, in the same way as in Example 3, at a circulation rate of 100 ml/min and a flux (a permeation rate) of 4.5 ml/min. Results are 0.09 EU/ml of pyrogens and a removal extent of 96.5% at a permeated liquid amount of 50 ml. The rabbit test shows an exothermic temperature (° C.) between 0.29 and 0.43, which is negative. A comparison by the PVA membrane results in a pyrogen content of 1.83 EU/ml and a removal extent of about 28%.

We claim:

1. A separating membrane for separating drugs from pyrogens having similar molecular weights, selectively absorbing a pyrogen and treating large quantities of liquid at a high speed while effectively lowering the pyrogen content thereof, said membrane comprising a nitrogen-containing compound and having a porous membrane structure with a pore size distribution such that at least 90% of particles having a size of 0.5 microns or larger are blocked by said membrane when it has a thickness of 0.1 mm or more, said membrane being liquid permeable so as to be able to absorb and remove phosphopolyols contained in a liquid while permitting the liquid to pass therethrough.

2. The membrane as claimed in claim 1, in which the compound is a nitrogen-containing cyclic compound.

3. The membrane as claimed in claim 1, in which the compound is a nitrogen-containing compound having an aliphatic chain group of 3 to 50 carbon atoms.

4. The membrane as claimed in claim 1, in which the compound is a nitrogen-containing cyclic compound with a pai electron system.

5. In a method for separating phosphopolyols from a liquid containing them, the improvement comprising passing said liquid through a separating membrane for separating drugs from pyrogens having similar molecular weights, selectively absorbing a pyrogen and treating large quantities of liquid at a high speed while effectively lowering the pyrogen content thereof, said membrane comprising a nitrogen-containing compound and having a porous membrane structure with a pore size distribution such that at least 90% of particles having a size of 0.5 microns or larger are blocked by said membrane when it has a thickness of 0.1 mm or more, said membrane being liquid permeable so as to be able to absorb and remove phosphopolyols contained in a liquid while permitting the liquid to pass therethrough.

6. The method as claimed in claim 5, in which the phosphopolyols are pyrogens.

7. The method as claimed in claim 5, in which the compound is a nitrogen-containing compound having a pai electron system.

8. The method as claimed in claim 5, in which the compound is a nitrogen-containing compound having an aliphatic chain group of 3 to 50 carbon atoms.

* * * * *